United States Patent
Nowak et al.

(10) Patent No.: US 6,906,117 B2
(45) Date of Patent: Jun. 14, 2005

(54) AZIRIDINOSILICONES AND THE USE THEREOF

(75) Inventors: Reinhold Nowak, Adelshofen (DE); Joachim Zech, Kaufering (DE); Peter Bissinger, Diessen (DE); Erich Wanek, Kaufering (DE); Gunther Eckhardt, Frieding (DE); Guenther Lechner, Woerthsee (DE)

(73) Assignee: 3M Espe AG, Seefeld (DE)

( * ) Notice: Subject to any disclaimer, the term of this patent is extended or adjusted under 35 U.S.C. 154(b) by 103 days.

(21) Appl. No.: 10/296,997
(22) PCT Filed: May 30, 2001
(86) PCT No.: PCT/EP01/06140
§ 371 (c)(1), (2), (4) Date: Jun. 4, 2003
(87) PCT Pub. No.: WO01/92373
PCT Pub. Date: Dec. 6, 2001

(65) Prior Publication Data
US 2004/0014924 A1 Jan. 22, 2004

(30) Foreign Application Priority Data
May 31, 2000 (DE) .......................... 100 26 857

(51) Int. Cl.$^7$ .......................... C08L 83/00; C08G 77/26
(52) U.S. Cl. .......................... 523/109; 528/27; 528/28; 528/38; 528/23; 524/266; 524/268; 524/588
(58) Field of Search ................ 524/266, 268, 524/588; 528/23, 27, 28, 38; 523/109

(56) References Cited

U.S. PATENT DOCUMENTS

| | | | |
|---|---|---|---|
| 3,453,242 A | | 7/1969 | Schmitt et al. |
| 3,700,716 A | * | 10/1972 | Berger et al. ............... 556/410 |
| 4,093,555 A | | 6/1978 | Schmitt et al. |
| 4,167,618 A | | 9/1979 | Schmitt et al. |

FOREIGN PATENT DOCUMENTS

| | | |
|---|---|---|
| DE | 3741575 | 6/1988 |
| DE | 3838587 | 5/1990 |
| DE | 4010281 | 10/1990 |
| DE | 4019249 | 8/1991 |
| DE | 4306997 | 9/1994 |
| DE | 19719438 | 11/1997 |

OTHER PUBLICATIONS

Abstract for SU 221293 A.*

* cited by examiner

Primary Examiner—Margaret G. Moore
Assistant Examiner—Marc S Zimmer
(74) Attorney, Agent, or Firm—Crowell & Moring LLP

(57) ABSTRACT

Arizidinosilicones of the general formula (1), wherein R1 represents H, C1–C12 alkyl, C2–C12 alkenyl, C2–C12 alkinyl, C7–C15 alkaryl, C7–C15 aralkyl, C3–C12 cycloalkyl and these groups can be substituted with Cl or F partially, completely or in a mixed manner and/or may contain 0 to 5 heteroatoms selected from O, N, S, R2 represents a group of the selection of R1 and/or R4, and R3 represents SiRl3 or SiR12R4, and wherein R4 represents formula (2), and A represents an (n+1) radical saturated, unsaturated or aromatic, linear, branched or cyclic hydrocarbon group that may contain 0 to 5 heteroatoms selected from O, N, S and that includes 1 to 18 carbon atoms, B is selected from O, S, NR1, D is selected from C(O)O, C(O)NR1, C(O), C(O)C(O), C(O)(CH2)m(C(O), C(S)NR1, CH2, E represents a diradical saturated or unsaturated, linear, branched or cyclic hydrocarbon group that may contain 0 to 5 heteroatoms selected from O, N, S and that includes 0 to 18 carbon atoms, a is 0 or 1, f is an integer from 2 to 1000, n, m is an integer from 1 to 10, and x, y, z each represents 0 or an integer, the sum of which should range between 1 and 10000, with the proviso that, if x is larger 0, y or z is smaller or equal x, preferably smaller or equal 0.05 times x, and especially preferred 0.02 times x. The invention also relates to the use of arizidinosilicones.

18 Claims, No Drawings

AZIRIDINOSILICONES AND THE USE THEREOF

BACKGROUND AND SUMMARY OF THE INVENTION

The invention relates to aziridinosilicones and to the use thereof, in particular in dental preparations.

For the purposes of this invention, the term aziridinosilicones is taken to mean oily or resinous polymeric siloxanes which have been functionalized with aziridino groups (analogous to the term "vinyl- or hydridosilicone oils" in A. Tomanek, Silicone & Technik [Silicones & Technology], Hanser 1990, p. 37).

High-precision elastic impression materials which are distinguished by high impression accuracy, high dimensional stability and good detail reproduction are, for example, materials based on agar, polysulfides, polyethers or addition-crosslinking silicones.

In the case of the addition-crosslinking silicone impression materials, curing is achieved by reaction of a polysiloxane containing vinyl end groups with a poly-siloxane containing SiH groups using platinum catalysts. The impressions obtained in this way are distinguished by very good elastic properties and high storage stabilities. These materials have always had the disadvantage of low hydrophilicity, which results in low drawing sharpness owing to a poor flow capacity.

In order to improve the hydrophilic behavior of silicone impression materials, hydrophilizing additives are added to the addition-crosslinking silicone impression materials. However, the better wettability achieved in this way is also accompanied by increased water absorption on contact with moist media, which can result in impaired dimensional stability and increased evolution of hydrogen.

In the case of the pure polyether materials, aziridine-containing substances are polymerized, as described in U.S. Pat. Nos. 3,453,242 and 4,093,555 or in DE-A-43 06 997. The sulfonium salts disclosed in U.S. Pat. No. 4,167,618, for example, are suitable for initiating the polymerization. Polyether impression materials prepared in this way have natural hydrophilic properties.

There have been various attempts to combine the hydrophilic properties of polyethers with the good elastic properties of silicones.

DE-A-37 41 575, DE-A-40 19 249, DE-A-40 10 281 and DE-A-38 38 587 describe materials based on a platinum-catalyzed addition reaction of an Si—H component with an unsaturated polyether. In contrast to addition-crosslinking silicones, the unsaturated polyether is generally the principal constituent, which provides the matrix with a hydrophilic characteristic.

DE-A-40 19 249 describes curable materials which, besides unsaturated polyethers containing alkenyl radicals, also comprise the products of the reaction of substituted polyethers of this type with oligosiloxanes containing at least two Si—H groups in the molecule and platinum catalysts as principal constituents.

In order to achieve an adequate storage stability, it is necessary to separate the reactive constituents spatially from one another. The Si—H compound and the platinum catalyst necessary for curing at room temperature cannot be combined in a paste since the Si—H compound would decompose.

During storage over a period of from several weeks to months, however, the problem arises that the catalyst component in which the platinum catalyst is combined with the unsaturated polyether has an unsatisfactory storage stability.

However, the dentist or technician needs to have access to an impression material which has a long storage stability and is guaranteed to be usable over a period of from several months to years.

DE-A-40 10 281 therefore proposes the addition of antioxidants in order to increase the storage stability. However, even this proposal results in unsatisfactory long-term storage stability.

DE-A-197 19 438 describes addition-crosslinking polyether impression materials which are distinguished by good storage stability of the catalyst component and of the base component and also of the cured dental material. These dental materials have the disadvantage of a low level of mechanical properties, meaning that they can only be employed to a restricted extent for dental impressions.

The object of the present invention is to provide curable materials which do not have the disadvantages of the prior art.

DETAILED DESCRIPTION OF THE INVENTION

This object has been achieved by N-alkylaziridinosilicones as the basis for the preparation of dental materials as described below.

The individual components of the materials prepared therefrom have good storage stability. For example, high impression accuracy is achieved on use as dental materials. In the cured state, these are distinguished by good mechanical properties.

The N-alkylaziridinosilicones according to the invention have the general structure of the formula (1) shown below:

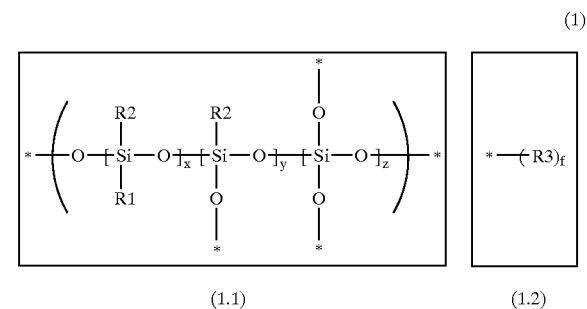

(1.1)  (1.2)

where:
R1=H, $C_1$–$C_{12}$-alkyl, $C_2$–$C_{12}$-alkenyl, $C_2$–$C_{12}$-alkynyl, $C_7$–$C_{15}$-alkaryl, $C_7$–$C_{15}$-aralkyl or $C_3$–$C_{12}$-cycloalkyl, and these radicals may be substituted partially, fully or in a mixed manner by Cl or F and/or may contain from 0 to 5 heteroatoms from the group consisting of O, N and S, and use is preferably made of H, methyl, ethyl, ethenyl, propenyl, phenyl, tolyl, 2-ethylphenyl or cyclohexenyl,
R2=a radical from the selection of R1 and/or R4, and
R3=$SiR1_3$ or $SiR1_2R4$, where R4=

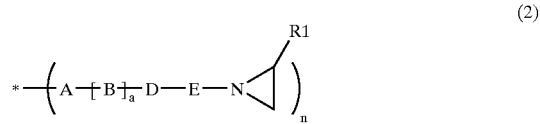

and

A=an (n+1)-valent saturated, unsaturated or aromatic, linear, branched or cyclic hydrocarbon radical, which may contain from 0 to 5 heteroatoms from the group consisting of O, N and S and comprises from 1 to 18 carbon atoms, preferably from 1 to 12 carbon atoms, B=selected from the group consisting of O, S and NR1, D=selected from the group consisting of C(O)O, C(O)NR1, C(O), C(O)C(O), C(O)(CH$_2$)$_m$(C(O), C(S)NR1 and CH$_2$, E=a divalent saturated or unsaturated, linear, branched or cyclic hydrocarbon radical, which may contain from 0 to 5 heteroatoms from the group consisting of O, N and S and comprises from 0 to 18 carbon atoms, preferably from 1 to 12 carbon atoms, a=0 or 1, f=an integer from 2 to 1000, preferably from 2 to 100, particularly preferably from 2 to 50, n and m=an integer from 1 to 10, preferably from 1 to 5, particularly preferably from 1 to 3, and x, y and z are each either 0 or integers whose sum is between 1 and 10,000, preferably between 1 and 1000 and particularly preferably between 10 and 500, where the mean molecular weight $M_n$ of the products can preferably be between 500 and 50,000 and particularly preferably between 1000 and 20,000, with the restrictions that, if x is greater than 0, y or z are less than or equal to x, preferably less than or equal to 0.05 times x and particularly preferably 0.02 limes x.

The symbol "*" in the formula (1.2) means that the valence marked in this way is linked to the positions marked "*" in fragment (1.1).

Of the respective x radicals of R2, up to 0.5 times x radicals are R4, and the others are R1.

In the case where y+z=0, linear polysiloxanes are present, and in the case where y+z>0, branched polysiloxanes are present, where the formula (1) should be taken to mean that in this case the polymer may contain both D and T and/or Q units in the context of silicone nomenclature, which may be in any position in the molecule and at the linking points of the T and Q units have D chains of any desired length whose total length is x D units.

Each mention of the radical R1 means merely a choice from the selection made under R1, different namings can mean different radicals R1 at each different substitution point and also on each recurring unit of a polymeric formula. This means that the structural unit —(SiOR1R2)$_x$— is intended to mean both homopolymers having a defined R1 and R2 and also copolymers of silicones with different radicals R1 and R2, but where x denotes the number of all silicon atoms covered thereby without regard to the choice made for radicals R1 and R2. An analogous situation applies correspondingly to the factor —SiR2(O*))$_y$— and the radical R3.

In general, no polymer-uniform polysiloxane basic chains are present. Depending on the preparation process, the polydispersity ($M_w/M_n$) is from 1.1 to 20 and preferably from 1.2 to 10.

The N-alkylaziridinosilicones according to the invention have molecular weights in the range from 500 to 50,000 g/mol, preferably from 1000 to 30,000 g/mol and particularly preferably in the range from 3000 to 20,000 g/mol. They have at least one and up to ten N-alkylaziridino groups in the molecule.

In order to establish the network structure desired in each case, the N-alkylaziridinosilicones used can have greatly different aziridino equivalent weights, where the range from 250 to 25,000 g/equivalent and particularly from 400 to 10,000 g/equivalent is preferred.

Preferred examples of the N-alkylaziridinosilicones according to the invention are those obtained by combination of preferred representatives of the formula (1) and formula (2) in the sense of the general formulae.

The linking of representatives of the formula (2) to those of the formula (1) is frequently accomplished by means of a hydrosilylation reaction. As is known to the person skilled in the art (Bogdan Marciniec "Comprehensive Handbook on Hydrosilylation"), this generally results in mixtures of the α- and β-adducts. In all formula examples, the β-adduct is shown, but the α-adduct is always also included.

Preferred representatives of the formula (1) are taken from the group consisting of linear siloxanes, comb-like silicones, T-branched siloxanes and MQ-silicone resins. Preferred representatives of these individual groups are the following:

Linear Siloxanes

For the following formulae of the terminally aziridino-functionalized silicones, all copolymers with dimethylsiloxane are also meant.

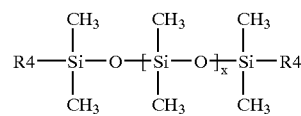

from: R1=methyl, R2=R1, x=0 to 500, R3=SiMe$_2$R4 (R4 see formula (2)), y, z=0, f=2

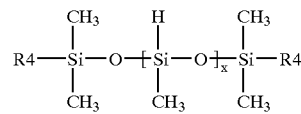

from: R1=methyl, R2=H, x=0 to 500, R3=SiMe$_2$R4 (R4 see formula (2)), y, z=0, f=2

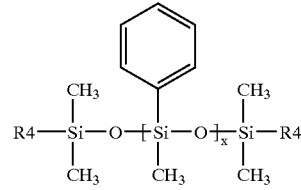

from: R1=methyl, phenyl, R2=R1, x=0 to 500, R3=SiMe$_2$R4 (R4 see formula (2)), y, z=0, f=2

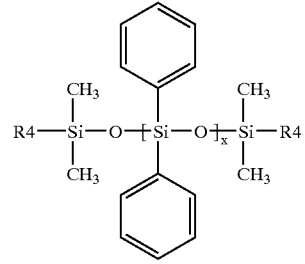

from: R1 methyl, phenyl, R2=R1, x=0 to 500, R3=SiMe₂R4 (R4 see formula (2)), y, z=0, f=2

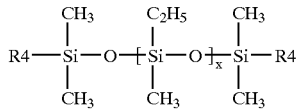

from: R1 methyl, ethyl, R2=R1, x=0 to 500, R3=SiMe₂R4 (R4 see formula (2)), y, z=0, f=2

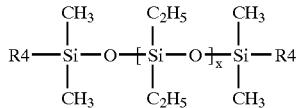

from: R1=methyl, ethyl, R2=R1, x=0 to 500, R3=SiMe₂R4 (R4 see formula (2)), y, z=0, f=2

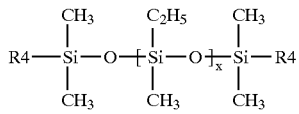

from: R1=methyl, vinyl, R2=R1, x=0 to 500, R3=SiMe₂R4 (R4 see formula (2)), y, z=0, f=2

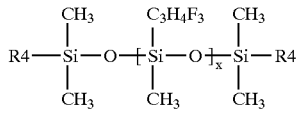

from: R1=methyl, 3,3,3-trifluoropropyl, R2=R1, x=0 to 500, R3=SiMe₂R4 (R4 see formula (2)), y, z=0, f=2

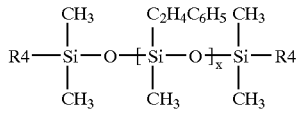

from: R1=methyl, phenylethylenyl, R2=R1, x=0 to 500, R3=SiMe₂R4 (R4 see formula (2)), y, z=0, f=2

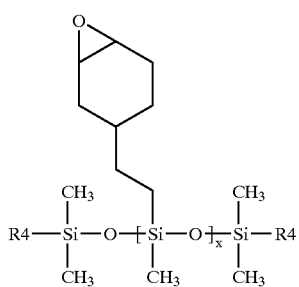

from: R1=methyl, epoxycyclohexylethylenyl, R2=R1, x=0 to 500, R3=SiMe₂R4 (R4 see formula (2)), y, z=0, f=2

Comb-Like Silicones

For the following formulae of silicones functionalized with pendant aziridino groups, all copolymers with dimethylsiloxane are also meant, with the number x of functionalized siloxane units being reduced by the proportion of dimethylsiloxane units.

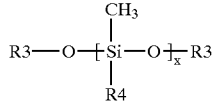

from: R1=methyl, R2=R4, x=0 to 500, R3=SiMe₂R4 (R4 see formula (2)) or SiR1₃(R1 methyl); y, z=0, f=1 to 100

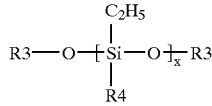

from: R1 ethyl, R2=R4, x=0 to 500, R3=SiMe₂R4 (R4 see formula (2)) or SiR1₃ (R1=methyl); y, z=0, f=1 to 100

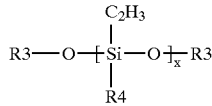

from: R1=vinyl, R2=R4, x=0 to 500, R3=SiMe₂R4 (R4 see formula (2)) or SiR1₃ (R1=methyl); y, z=0, f=1 to 100

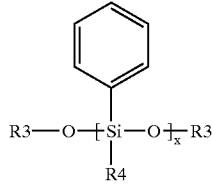

from: R1=phenyl, R2=R4, x=0 to 500, R3=SiMe₂R4 (R4 see formula (2)) or SiR1₃ (R1=methyl); y, z=0, f=1 to 100

T-Branched Siloxanes

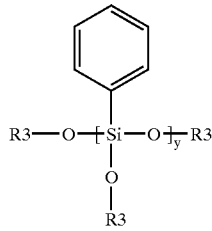

from: R1=methyl, R2=R4, x=0, R3=SiMe₂R4 (R4 see formula (2)) or SiR1₃ (R1=methyl); y=1–500, z=0, f=1 to 100

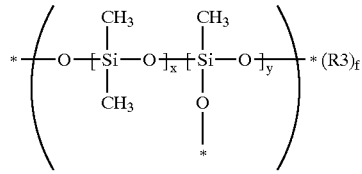

from: R1=methyl, R2=R1, x=0–500, y=1–25; R3=SiMe₂R4 (R4 see formula (2)) or SiR1₃ (R1=methyl); z=0, f=1 to 100

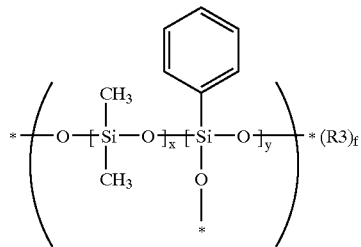

from: R1=methyl, R2=phenyl, x=0–500, y=1–25; R3=SiMe₂R4 (R4 see formula (2)) or SiR1₃ (R1=methyl); z=0, f=1 to 100

MQ-Silicone Resins

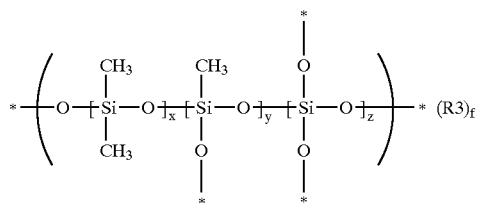

from: R1=methyl, R2=R1, x=0 to 500, y=0 to 25; z=1 to 25; R3=SiMe₂R4 (R4 see formula (2)) or SiR1₃ (R1=methyl); f=1 to 100

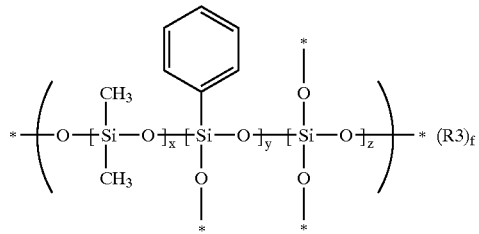

from: R1=methyl, R2=phenyl, x=0 to 500, y=0 to 25; z=1 to 25; R3=SiMe₂R4 (R4 see formula (2)) or SiR1₃ (R1=methyl); f=1 to 100.

Besides the N-alkylethyleneimine derivatives preferred representatives of the formula (2) are also the N-alkylpropyleneimine derivatives:

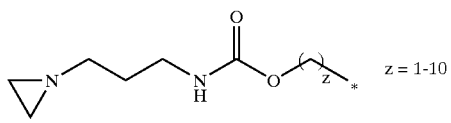

from: A=(CH₂)$_z$; B=O; D=C(O)NR1 (where R1=H); E=1,3-propanediyl; a=1; n=1

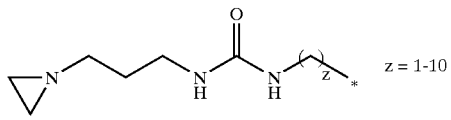

from: A=(CH₂)$_z$; B=NH; D=C(O)NR1 (where R1=H); E=1,3-propanediyl; a=1; n=1

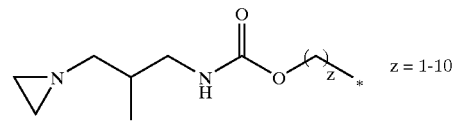

from: A=(CH₂)$_z$; B=O; D=C(O)NR1 (where R1=H); E=2-methyl-1,3-propanediyl; a=1; n=1

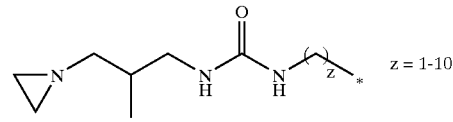

from: A=(CH₂)$_z$; B=NH; D=C(O)NR1 (where R1=H); E=2-methyl-1,3-propanediyl; a=1; n=1

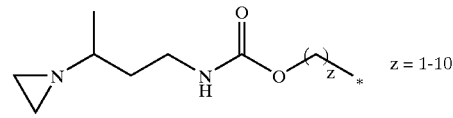

from: A=(CH₂)$_z$; B=O; D=C(O)NR1 (where R1=H); E=1,3-butanediyl; a=1; n=1

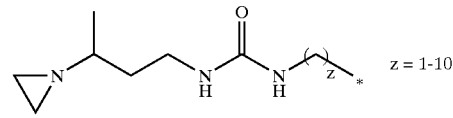

from: A=(CH₂)$_z$; B=NR1 (R1=H); D=C(O)NR1 (where R1=H); E=1,3-butanediyl; a=1; n=1

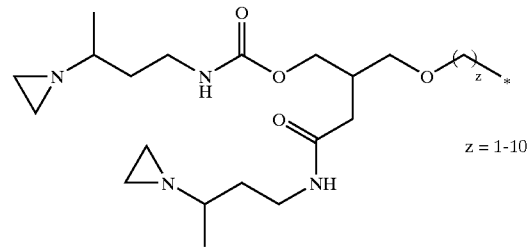

from: A=3-oxaheptane-1,2,7-triyl (for z=3); B=O; D=C(O)NR1 (where R1=H); E=1,3-butanediyl; a=1; n=2

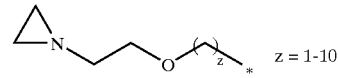

from: A=(CH₂)$_z$; B=O; D=CH₂; E=methanediyl; a=1; n=1

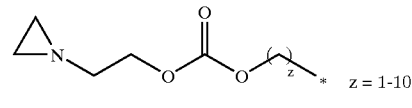

from: A=(CH₂); B=O; D=C(O)O; E=1,2-ethanediyl; a=1; n=1

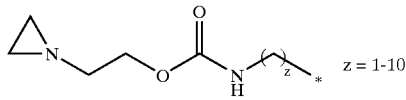

from: A=(CH₂)_z; B=O; D=C(O)O; E=1,2-ethanediyl; a=1; n=1

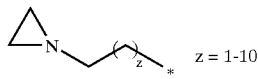

from: A=(CH₂)_{z+1}; D=CH₂; E=CH₂; a=0; n=1

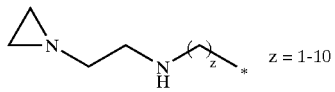

from: A=(CH₂)_z; B=NH; D=CH₂; E=1,2-ethanediyl; a=1; n=1

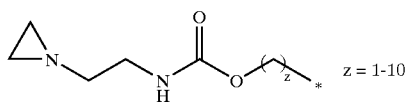

from: A=(CH₂)_z; B=NH; D=C(O)O; E=1,2-ethanediyl; a=1; n=1

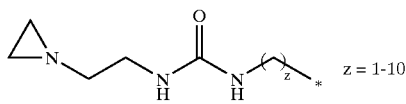

from: A=(CH₂)_z; B=NH; D=C(O)NH; E=1,2-ethanediyl; a=1; n=1

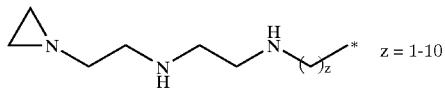

from: A=(CH₂)_z; B=NH; d=CH₂; E=2-aza-1,4-butanediyl; a=1; n=1

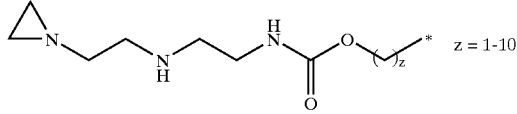

from: A=(CH₂)_z; B=NH; D=C(O)O; E=2-aza-1,4-butanediyl; a=1; n=1

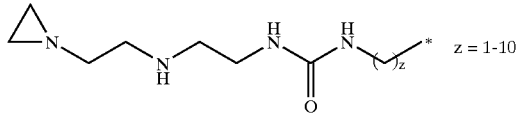

from: A=(CH₂)_z; B=NH; D=C(O)NH; E=2-aza-1,4-butanediyl; a=1; n=1

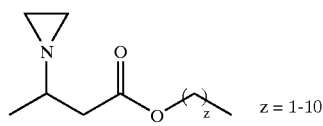

from: A=(CH₂)_z; B=O; D=C(O); E=2-methyl-1,2-propanediyl; a=1; n=1

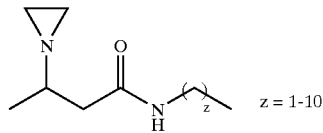

from: A=(CH₂)_z; B=NH; D=C(O); E=2-methyl-1,2-propanediyl; a=1; n=1

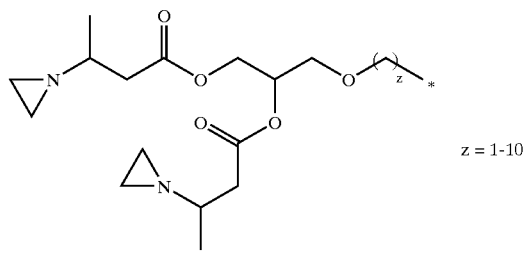

from: A=3-oxaheptane-1,2,7-triyl; B=O; D=C(O); E=2-methyl-1,2-propanediyl; a=1; n=2

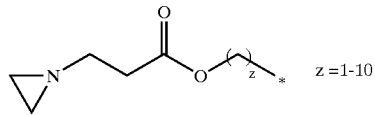

from: A (CH₂)_z; B=O; D=C(O); E=1,2-ethanediyl; a=1; n=1

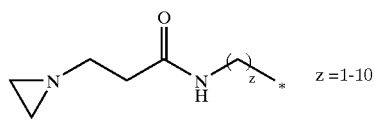

from: A=(CH₂)_z; B=NH; D=C(O); E=1,2-ethanediyl; a=1; n=1

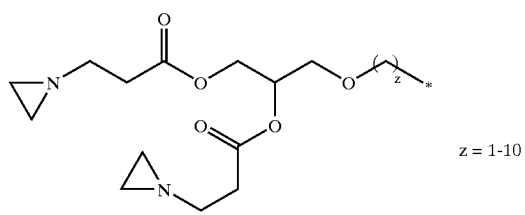

from: A=3-oxaheptane-1,2,7-triyl; B=O; D=C(O); E=1,2-ethanediyl; a=1; n=2

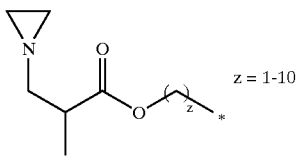

z = 1-10 from: A=(CH$_2$)$_z$; B=O; D=C(O); E=1-methyl-1,2-propanediyl; a=1; n=1

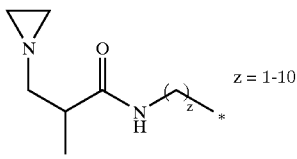

z = 1-10 from: A=(CH$_2$)$_z$; B=NH; D=C(O); E=1-methyl-1,2-propanediyl; a=1; n=1

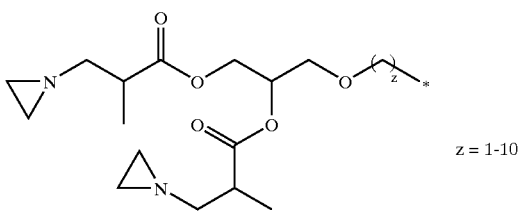

z = 1-10 from: A=3-oxaheptane-1,2,7-triyl; B=O; D=C(O); E=1,-methyl-1,2-propanediyl; a=1; n=2

In principle, the preparation of the N-alkylaziridinosilicones according to the invention is carried out by converting a commercially available functionalized polysiloxane into the aziridinosilicone in one or more steps. Instead of employing the commercially available functionalized polysiloxanes as such, they can also be modified alone, as a mixture and/or as a mixture with silicone raw materials by equilibration, polymerization, copolymerization, depolymerization, etc., in a known manner (see P. Kochs in Houben-Weyl, Vol. E20, p. 2219 ff.) and only then functionalized to give the aziridinosilicone. A multiplicity of representatives of functionalized silicone oils of this type can be found, for example, in the "Reactive Silicones" catalogue from Gelest. However, they can also be prepared in accordance with procedures known from the literature (H. R. Kricheldorf (Ed.), "Silicon in Polymer Synthesis", Springer, 1996, Chapt. 3). Particularly suitable for functionalization are hydrido-, acrylic-, methacrylic-, vinyl-, hydroxyalkyl- and aminoalkyl-functionalized siloxanes.

Aziridinosilicones can be prepared therefrom, for example via chlorooxalates or chloroformates, with in some cases activated amides, such as imidazolides, being prepared as intermediates from the chlorooxalates or chloroformates. Suitable aziridino components are, for example, aziridinoethanol (Acros) or other hydroxy- or amino-functional aziridino compounds. Another route consists in adding aziridine onto activated double bonds of correspondingly functionalized silicones.

Besides these methods for the synthesis of aziridino compounds, a multiplicity of possible synthesis variants for building up and derivatizing or modifying aziridino compounds is found in the following monographs and in the references cited therein. The preferred representatives of the aziridinosilicones and, if necessary, their precursors can be prepared by the procedures described therein, with some of these methods needing to be adapted appropriately by the person skilled in the art: R. C. Elderfield, "Heterocyclic compounds", Vol. 1, pp. 61–77, Wiley, 1950; Houben-Weyl, "Methoden der Organischen Chemie" [Methods of Organic Chemistry], Vol. XI/2, pp. 223–264, Thieme, 1958; O. C. Dermer, G. E. Ham, "Ethylenimine and other Aziridines", in particular pp. 106–205 and pp. 340–393, Academic Press, 1969; Houben-Weyl, "Methoden der Organischen Chemie" [Methods of Organic Chemistry], Vol. E16c, pp. 370–667, Thieme, 1992; Ulmanns Encyclopedia of Industrial Chemistry, 5th Ed., Vol. A3, pp. 239–243.

The invention furthermore relates to curable materials based on N-alkylaziridinosilicones according to the invention, in particular two-component dental materials, which comprise, after mixing of the components, in each case based on 100 parts by weight:

(A) from 30 to 97 parts by weight, preferably from 40 to 89 parts by weight, particularly preferably from 45 to 80.5 parts by weight, of at least one N-alkylaziridinosilicone having molecular weights in the range from 500 to 50,000 g/mol and aziridino equivalent weights in the range from 250 to 25,000 g/equivalent (B) from 1 to 10 parts by weight, preferably from 1 to 5 parts by weight, particularly preferably from 1.5 to 3 parts by weight, of starter substances which are suitable for effecting curing of the N-alkylaziridinosilicones, (C) from 1 to 35 parts by weight, preferably from 5 to 25 parts by weight, particularly preferably from 8 to 20 parts by weight, of organic diluents, (D) from 1 to 50 parts by weight, preferably from 5 to 40 parts by weight, particularly preferably from 10 to 30 parts by weight, of modifiers, including fillers, dyes, pigments, thixotropy agents, flow improvers, polymeric thickeners, surface-active substances, odor substances and flavor substances.

The preparation produced by homogeneous mixing of the catalyst component and the base component has, for example, a pot life at room temperature of between 0.5 and 10 minutes, and the preparation prepared in this way cures, for example, within a period of from one to 20 minutes at a temperature in the range from 23 to 36° C. to give an elastically deformable material having a Shore A hardness of at least 20.

In the case of two-component materials, constituents (A) to (D) are divided, before mixing, amongst the base and catalyst components in such a way that all of constituent (A) is present in the base component and all of constituent (B) is present in the catalyst component. Constituents (C) and (D) may be present proportionately in the components.

The proportions of the individual components (A) to (D) should be adjusted within the stated limits in such a way that favorable processability with respect to mixing ratio and flow behavior is ensured and the criteria for the desired pot life, the curing time and the mechanical properties of the cured material are observed.

The mixing ratio can be set in a broad range via the composition of the two components, with mixing ratios of catalyst component to base component of from 1:1 to 1:5 having proven particularly practicable.

Constituent (A) comprises the N-alkylaziridinosilicones according to the invention. The use of mixtures of N-alkylaziridinosilicones having different molecular weights and aziridino equivalent weights is possible and is utilized to adjust the properties of the dental materials.

Suitable starter substances as per constituent (B) of the mixed preparation are a series of compounds if they meet the criteria regarding setting rate and resultant elastomer properties.

Thus, suitable starter substances for use in two-component impression materials based on the polyether derivative described above are those which facilitate curing of the mixed preparation in a period of from 1 to 20 minutes to give an elastic solid, where this solid meets the requirements of an elastic impression material in accordance with DIN/EN 2482 and has a Shore A hardness (DIN 53505) of at least 20 after a storage time of 24 hours.

Suitable starters as per constituent (B) of the catalyst component are many of the known starters. Use is advantageously made of starters or starter systems which allow simple adjustment of the course of curing, do not produce any side effects and enable the requisite level of the mechanical properties to be achieved reproducibly.

DE-C-914 325 proposes the use of oxonium, ammonium and sulfonium salts as starter substances.

A comprehensive review of the starter substances used for the curing of N-alkylaziridino compounds is given in O. C. Dermer, G. E. Ham, "Ethylenimine and other aziridines", Academic Press (1969).

Accordingly, a large number of classes of compound and compounds have proven to be suitable in principle as polymerization initiators. However, it is very difficult in practical application of cationic polymerization of aziridinopolyethers to establish the desired course of setting with an adequately long pot life and fast final curing. This aim can be achieved through the use of specific trisalkylsulfonium salts, as described, for example, in EP-A-0 110 429.

The criteria of curing rate and the properties of the elastic solid can in principle be achieved using specific trisalkylsulfonium salts.

The patent application DE-100 18 918 describes starters which provide the catalyst component with a merely low acid degree and which facilitate a readily adjustable, relatively long pot life after the base component and catalyst component have been mixed.

Starter systems of this type are suitable for curing the base pastes according to the invention at the requisite rate. Through their use, the desired properties of the elastic solid can be achieved.

Patent application DE-19942459 describes elastomer materials having an improved catalyst component which are distinguished by increased extensibility. According to this invention, boric acid complexes are employed as starters. These starters have proven particularly successful for the curing of the N-alkylaziridino-polyethers according to the present invention and are employed with advantages compared with other starter systems.

The organic diluents as per constituent (C) are polyether-polyols, such as polypropylene glycols or mixed polyetherols containing tetrahydrofuran and/or ethylene oxide and/or propylene oxide units, polyester-polyols, such as polycaprolactone-diols and polycaprolactone-triols, polycarbonate-diols, aliphatic esters, oils, fats, waxes, aliphatic hydrocarbons, araliphatic hydrocarbons and mono- or polyfunctional esters of polybasic acids, such as, for example, phthalic acid or citric acid, or esters or amides of alkylsulfonic acids and arylsulfonic acids.

It is also possible to employ liquid organosiloxanes, such as polydimethylsiloxanes of various chain lengths. Com pounds as per this constituent which can advantageously be employed conform to the following general structures:

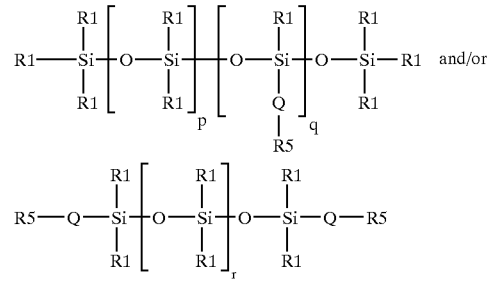

where
Q=an α,ω-valent polyether chain of the formula (3):

 (3);

R5=OH, OR1, O—C(O)—R1 or O—C(O)—NHR1;
g=from 2 to 20, preferably from 2 to 10, particularly preferably from 2 to 7;
h=from 1 to 1000, preferably from 1 to 500, particularly preferably from 1 to 200;
p=an integer from 1 to 1000, preferably from 3 to 500;
q=an integer from 1 to 50, preferably from 3 to 10;
r=an integer from 1 to 1000, preferably from 1 to 500.

Depending on the preparation process, the polydispersity of the polyether blocks can be from 1.1 to 20 and preferably from 2 to 10.

The polyether block can be a homopolymer, a copolymer or a terpolymer. The mixed polymers can have an alternating or random structure or have alternating and random mixed polyether blocks, which are optionally connected to homopolymer polyether blocks.

Preferred polyether blocks are polytetrahydrofuran, polypropylene oxide, random copolymers of ethylene oxide and tetrahydrofuran, of propylene oxide and tetrahydrofuran, of ethylene oxide and propylene oxide, block copolymers of ethylene oxide and propylene oxide and random terpolymers of ethylene oxide, propylene oxide and tetrahydrofuran.

Modifiers corresponding to constituent (D) are added to the catalyst component and the base component.

These modifiers are usually finely divided fillers, such as aluminosilicates, precipitated silicic acids, quartz flour, wollastonite, mica flour and diatomaceous earth, as well as dyes and pigments, whose addition facilitates better assessment of the mixing quality and reduces the risk of misidentification, thixotropic agents, such as finely disperse silicic acids, and other additives which influence the flow behavior, such as polymeric thickeners, furthermore surface-active substances for adjusting the flow behavior, and odor substances and flavor substances.

The materials according to the invention are particularly suitable as dental impression materials, bite registration materials, modeling materials, temporary filling materials, materials for the production of temporary crowns and bridges, and duplicating materials.

Depending on the composition of the catalyst component and the base component, they can also be employed for bonding substrates, for sealing, coating and encapsulation.

The two components can be dispensed visually, such as by comparison of extrudate lengths, by weight, via pre-dispensed pack units and subsequent hand mixing, from double-chamber cartridges with a static mixing tube or by means of volume dispensing units with downstream static or dynamic mixer.

In order to achieve optimum results, high mixing quality is necessary. By contrast, the tolerance in the mixing ratio is generally relatively large and can, for example at a pre-specified ratio of catalyst component to base component of 1:5, cover the range from 0.75 to 1.25:5 without use-restricting property changes being evident.

In the taking of dental impressions, the good flow behavior against the moist tooth and the moist gums and the low sensitivity of the impression precision to saliva and blood proves to be a major advantage.

It has been found that impression materials based on the substances according to the invention cannot bond to impression materials or modeling materials based on A-silicones and/or polyethers. This opens up the possibility of using the substances according to the invention to prepare an in-situ impression material in which the cured impression can be cast with an A-silicone without having to be isolated first.

The invention also relates to containers and mixing devices containing the materials, in particular dental materials, prepared from the preparations according to the invention, such as cartridges, bags, impression trays, static and dynamic mixers and mixing equipment.

The invention is explained in greater detail by the following examples without it being intended that it is restricted thereby.

EXAMPLES

Synthesis Example 1

Preparation of an Aziridinosilicone from a Methacrylate-Terminated Silicone Oil

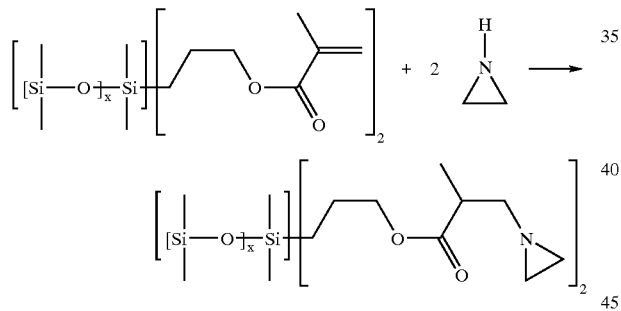

100 g of DMS-R28 silicone oil (Gelest) [M=5000, 0.02 mol] are mixed with 50 ml of toluene and 3.44 g of aziridine (Ferak) [M=43.07, 0.08 mol]. The mixture is heated to 50° C., after five hours increased to 100° C. and held at 100° C. until a check of the conversion by IR spectroscopy indicates the disappearance of the C=C double bond. After conventional work-up and product isolation, 100 g of a clear, colorless aziridinosilicone remain.

Synthesis Example 2

Preparation of an Aziridinosilicone from an Acrylate-Terminated Silicone Oil

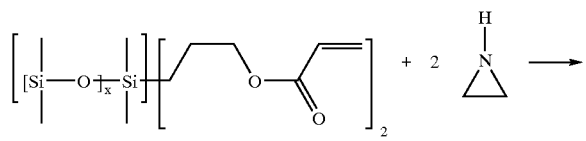

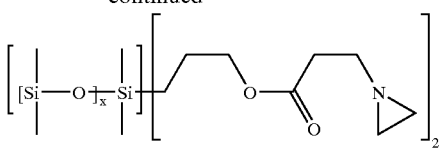

100 g of DMS-U22 silicone oil (Gelest) [M=1100, 0.091 mol] are mixed with 50 ml of toluene. At 30° C., 31.3 g of aziridine [M 43.07, 0.73 mol] are added dropwise. The mixture is heated to 50° C., after five hours increased to 100° C. and held at 100° C. until a check of the conversion by IR spectroscopy indicates the disappearance of the C=C double bond. After conventional work-up and product isolation, 110 g of a clear, colorless aziridinosilicone remain.

Synthesis Example 3

Preparation of an Aziridinosilicone from a Silicone Oil Containing Pendant Acrylate Groups

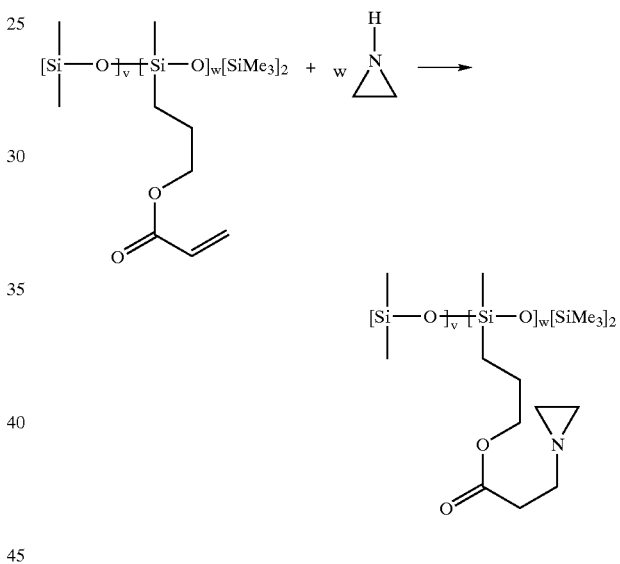

100 g of UMS-182 silicone oil (Gelest) [w=0.18*(v+w), 0.209 mol of acrylate groups] are mixed with 50 ml of toluene. At 30° C., 18.01 g of aziridine [M=43.07; 0.418 mol] are added dropwise. The mixture is heated to 50° C., after 5 hours increased to 100° C. and held at 100° C. until a check of the conversion by IR spectroscopy indicates the disappearance of the C=C double bond. After conventional work-up and product isolation, 105 g of a clear, colorless aziridino-silicone remain.

Examples of the preparation of dental materials are described below. With the aid of laboratory compounders, the catalyst components K1 to K3 described were prepared on a 100 g scale. The base components described in Table 1 were prepared on a 500 g scale.

Table 2 shows the mixtures investigated using the catalyst components described and the base component described in Table 1 in the weight ratio indicated in each case.

The mixtures in Table 2 were prepared by mixing with a spatula on the mixing block within 30 seconds and employed to determine the properties shown in Table 2.

Preparation of the Catalyst Components

Catalyst component K1

44 g of acetyl tributylcitrate (as per constituent (C)) were introduced into a laboratory compounder, and 20 g of β-(S-lauryl-S-ethylsulfonium)butyronitrile fluoroborate (see U.S. Pat. No. 4,167,618, as per constituent (B)) were dissolved therein. 12 g of diatomaceous earth (as per constituent (D)) and 24 g of pyrogenic silicic acid (HDK H 2000, Wacker, as per constituent (D)) were incorporated into this mixture.

Catalyst component K2

61.1 g of a poly(ethylene, propylene) glycol having a molecular weight of 3400 g/mol were introduced into a laboratory compounder, and 21 g of a hydrophobicized precipitated silicic acid (Sipernat D 17, Degussa, as per constituent (D)) were added in portions.

9.9 g of p-toluenesulfonic acid monohydrate (as per constituent (B)) were dissolved in 5 g of distilled water and added to the paste-form mixture. After homogenization, a paste consisting of 2 g of zinc oxide (as per constituent (B)) and 1 g of poly(ethylene, propylene) glycol (as per constituent (C)) having a molecular weight of 3400 g/mol was added. The paste was compounded for a further hour after the final addition.

Catalyst component K3

19 g of hydrophobicized precipitated silicic acid (Sipernat D 17, Degussa, as per constituent (D)) were incorporated into 31 g of a polypropylene oxide diol (as per constituent (C)) having a molecular weight of 2000 g/mol in a laboratory compounder. The solution of a complex compound (as per constituent (B), prepared from 3.6 g of boric acid and 17 g of salicyl alcohol, in 29.4 g of polypropylene oxide diol (as per constituent (B)) was added to this paste-form mixture, and the paste was compounded for one hour.

TABLE 1

Composition of the base components

| Compound | As per constituent | B1 | B2 | B3 | B4 | B5 |
|---|---|---|---|---|---|---|
| | | % by weight | | | | |
| Aziridinosilicone as per Synthesis Example 1 | (A) | 59.1 | 27.2 | 49.7 | — | 21.7 |
| Aziridinosilicone as per Synthesis Example 2 | (A) | — | 33.7 | — | 31.7 | 14.7 |
| Aziridinosilicone as per Synthesis Example 3 | (A) | — | — | 11.2 | 20.9 | 20.1 |
| Dimethylsiloxane AK 50 having a viscosity of 50 mPas | (C) | 3.9 | 6.8 | 3.10 | 5.70 | 5.50 |
| Dimethylsiloxane AK 5000 having a viscosity of 5000 mPas | (C) | 6.3 | 9.9 | — | — | 6.0 |
| Quartz powder (Silbond TST 600, Frechen) | (D) | — | — | 25.3 | 40.0 | 32.0 |
| Diatomaceous earth | (D) | 30.7 | 21.7 | 10.7 | — | — |
| Silicone-polyether block polymer (Silwet L 7280) | (C) | — | 0.7 | — | 1.7 | — |

The base components according to the invention as shown in Table 1 were distinguished by very good storage stability.

Thus, the samples stored at 36° C. for a period of 9 months would still be processed without problems with the stated catalyst components and gave mechanical properties of the elastomer solid which differed by less than 15% from the values measured at the beginning of storage.

TABLE 2

Elastomer materials according to the invention using catalyst components 1 to 3 and base components as per Table 1 and properties determined.

| | Use Example No. | | | | | |
|---|---|---|---|---|---|---|
| | 1 | 2 | 3 | 4 | 5 | 6 |
| Catalyst component (K) | K2 | K3 | K2 | K1 | K2 | K3 |
| Base component (B) | B1 | B2 | B3 | B4 | B5 | B1 |
| Mixing ratio (by weight) (K):(B) | 1:4.7 | 1:5.0 | 1:5.0 | 1:4.3 | 1:5.1 | 1:5.0 |
| Pot life at 23° C.[a] (minutes) | 1.7 | 1.0 | 1.5 | 2.1 | 1.7 | 1.2 |
| End of curing at 23° C.[b] (minutes) | 5.3 | 3.7 | 3.9 | 7.0 | 5.5 | 4.1 |
| Elongation at break (%)[a] | 72 | 112 | 79 | 62 | 51 | 100 |
| Tear strength (MPa)[a] | 0.82 | 0.75 | 0.92 | 0.69 | 0.87 | 1.03 |
| Shore A hardness after 24 hours in accordance with DIN 53505 | 42 | 39 | 47 | 49 | 52 | 43 |

[a] According to DIN/EN 4823
[b] The end of curing is defined as the time at which an elastic solid which has no surface tack is present a) According to DIN/EN 4823 b) The end of curing is defined as the time at which an elastic solid which has no surface tack is present All mixtures of Use Examples 1 to 6 according to the invention (Table 2) met the requirements of an elastic impression material according to DIN/EN 2482 and resulted in moldings which had a Shore A hardness (see Table 2) of significantly greater than 20 after a storage time at room temperature of 24 hours.

What is claimed is:

1. An N-alkylaziridinosilicone of the formula:

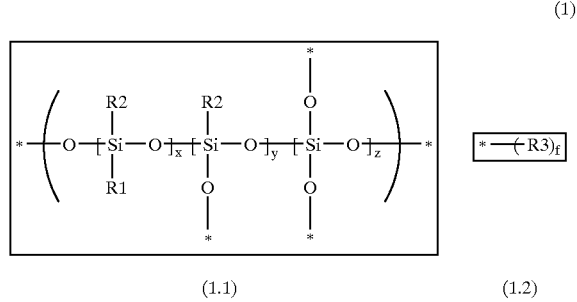

(1.1)        (1.2)

wherein:

R1=H, $C_1-C_{12}$-alkyl, $C_2-C_{12}$-alkenyl, $C_2-C_{12}$-alkynyl, $C_7-C_{15}$-alkaryl, $C_7-C_{15}$-aralkyl or $C_3-C_{12}$-cycloalkyl, and these radicals may be substituted partially, fully or in a mixed manner by Cl or F and/or may contain from 0 to 5 heteroatoms from the group consisting of O, N and S;

R2=a radical from the selection of R1 and/or R4; and

R3=$SiR1_3$ or $SiR1_2R4$;

wherein R4=

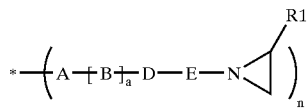
(2)

and

A=an (n+1)-valent saturated, unsaturated or aromatic, linear, branched or cyclic hydrocarbon radical, which may contain from 0 to 5 heteroatoms from the group consisting of O, N and S and comprises from 1 to 18 carbon atoms;

B=selected from the group consisting of O, S and NR1;

D=selected from the group consisting of C(O)O, C(O) NR1, C(O), C(O)C(O), C(O)(CH$_2$)$_m$(C(O), C(S) NR1 and CH$_2$;

E=a divalent saturated or unsaturated, linear, branched or cyclic hydrocarbon radical, which may contain from 0 to 5 heteroatoms from the group consisting of O, N and S and comprises from 0 to 18 carbon atoms;

a=0 or 1;

f=an integer from 2 to 1000;

n and m=an integer from 1 to 10; and x, y and z are each either 0 or integers whose sum is between 1 and 10,000;

wherein if x is greater than 0, y or z are less than or equal to x.

2. The N-alkylaziridinosilicone of claim 1, wherein if x is greater than 0, y or z are less than or equal to 0.05 times x.

3. The N-alkylaziridinosilicone of claim 1, wherein if x is greater than 0, y or z are less than or equal to 0.02 times x.

4. A curable material based on N-alkylaziridinosilicone of claim 1, which, after mixing of the components, comprises, based on 100 parts by weight:

(A) from 30 to 97 parts by weight of at least one N-alkylaziridino block copolymer having molecular weights in the range from 500 to 50,000 g/mol and aziridino equivalent weights in the range from 250 to 25,000 g/equivalent, (B) from 1 to 10 parts by weight of starter substances which are suitable for effecting curing of the N-alkylaziridino block copolymers, (C) from 1 to 35 parts by weight of organic diluents, and (D) from 1 to 50 parts by weight of modifiers.

5. A two-component dental material comprising the base component of claim 1 and a catalyst component, where the material produced by homogeneous mixing of the catalyst component and the base component has a pot life at room temperature of between about 0.5 and about 10 minutes, and the material cures within a period of from about 1 to about 20 minutes at a temperature in the range from about 23 to about 36° C. to give an elastically deformable material having a Shore A hardness of at least 20.

6. The N-alkylaziridinosilicone of claim 1, comprising an N-alkyl aziridinosilicone having from 1 to 10 N-alkylaziridino groups per molecule, where the N-alkylaziridinosilicone has a molecular weight in the range from 500 to 50,000 g/mol.

7. The curable material of claim 4, wherein said organic diluents comprise organopolysiloxanes having polyalkylene oxide blocks that conform to the following formulae:

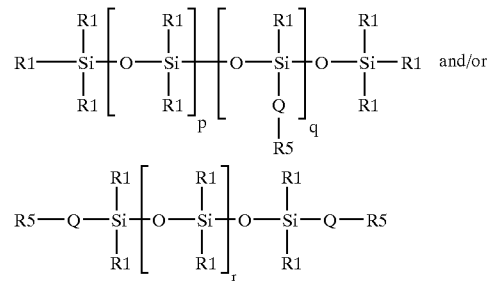 and/or where:

Q=an α,ω-valent polyether chain of the formula (3):

(3);

wherein

R5=OH, OR1, O—C(O)—R1 or O—C(O)—NHR1;

g=from 2 to 20;

h=from 1 to 1000;

p=an integer from 1 to 1000;

q=an integer from 1 to 50; and r=an integer from 1 to 1000.

8. The curable material of claim 4, wherein said starter substances comprise trisalkylsulfonium salts.

9. The curable material of claim 4, wherein said starter substances comprise Brönsted acids.

10. The curable material of claim 9, wherein the Brönsted acids acidity has been reduced by antiacids.

11. The curable material of claim 4, wherein starter substances comprise at least one boric acid complex.

12. A process of using the N-alkylaziridinosilicone of claim 1 comprising preparing a curable material.

13. A process of using the N-alkylaziridinosilicone of claim 1 comprising preparing a dental material.

14. A process of using the N-alkylaziridinosilicone of claim 1 comprising bonding, coating, or encapsulating substrates.

15. The process of claim 14, further comprising using dental impression materials, bite registration materials, modeling materials, temporary filling materials, materials for the production of temporary crowns and bridges, and duplicating materials.

16. A containing at least the N-alkylaziridinosilicone of claim 1.

17. A containing at least the curable material of claim 4.

18. A containing at least the dental material of claim 5.

* * * * *

UNITED STATES PATENT AND TRADEMARK OFFICE
CERTIFICATE OF CORRECTION

PATENT NO. : 6,906,117 B2  Page 1 of 2
APPLICATION NO. : 10/296997
DATED : June 14, 2005
INVENTOR(S) : Reinhold Nowak It is certified that error appears in the above-identified patent and that said Letters Patent is hereby corrected as shown below:

Column 1
Line 22, delete "poly-siloxane" and insert -- polysiloxane --, therefor.

Column 2
Lines 61-61, delete " 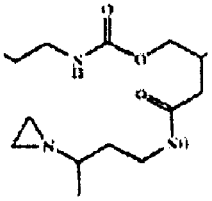 " and insert -- 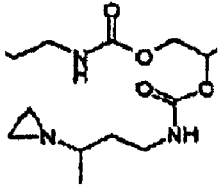 --, therefor.

Column 3
Line 30, delete "limes" and insert -- times --, therefor.

Column 5
Line 1, delete "R1 methyl," and insert -- R1=methyl, --, therefor.
Line 10, delete "R1 methyl," and insert -- R1=methyl, --, therefor.

Column 8
Lines 41-49, delete " 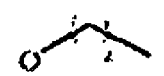 " and insert --  --therefor

Column 9
Line 1, delete "A=(CH$_2$);" and insert -- A=(CH$_2$)$_z$;--, therefor.
Line 49, delete "d=CH$_2$;" and insert -- D=CH$_2$; --, therefor.

Column 10
Lines 6-9, delete " 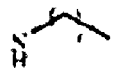 " and insert -- 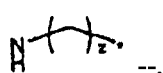 --, therefor.

Lines 16-19, delete "  " and insert --  --, therefor.

Column 16
Line 12, delete "[M 43.07," and insert -- [M=43.07, --, therefor.
Line 55, delete "aziridino-silicone" and insert -- aziridinosilicone --, therefor.

Column 18
Line 66, in Claim 1, delete "R4;" and insert -- R4. --, therefor.

UNITED STATES PATENT AND TRADEMARK OFFICE
CERTIFICATE OF CORRECTION

PATENT NO.        : 6,906,117 B2
APPLICATION NO.   : 10/296997
DATED             : June 14, 2005
INVENTOR(S)       : Reinhold Nowak It is certified that error appears in the above-identified patent and that said Letters Patent is hereby corrected as shown below:

Column 19
Lines 3-7, in Claim 1, delete "  " and insert -- ... --, therefor.

Column 20
Line 54, in Claim 16, after "A" insert -- container --.
Line 56, in Claim 17, after "A" insert -- container --.
Line 57, in Claim 18, after "A" insert -- container --.

Signed and Sealed this

Twenty-seventh Day of May, 2008

JON W. DUDAS
*Director of the United States Patent and Trademark Office*